(12) United States Patent
Yang et al.

(10) Patent No.: US 11,590,168 B2
(45) Date of Patent: Feb. 28, 2023

(54) CHIMERIC ANTIGEN RECEPTOR COMPRISING CO-STIMULATORY RECEPTOR AND APPLICATION THEREOF

(71) Applicant: SHANGHAI LONGYAO BIOTECHNOLOGY INC., LTD., Shanghai (CN)

(72) Inventors: Xuanming Yang, Shanghai (CN); Yangxin Fu, Shanghai (CN); Xin Wang, Shanghai (CN); Shengqin Ye, Shanghai (CN); Fanlin Li, Shanghai (CN); Huihui Zhang, Shanghai (CN)

(73) Assignee: Shanghai Longyao Biotechnology Inc., Ltd., Shanghai (CN)

( * ) Notice: Subject to any disclaimer, the term of this patent is extended or adjusted under 35 U.S.C. 154(b) by 19 days.

(21) Appl. No.: 17/126,966

(22) Filed: Dec. 18, 2020

(65) Prior Publication Data
US 2021/0169932 A1 Jun. 10, 2021

Related U.S. Application Data

(63) Continuation of application No. PCT/CN2019/077922, filed on Mar. 13, 2019.

(30) Foreign Application Priority Data

Jun. 20, 2018 (CN) .......................... 201810636409.0

(51) Int. Cl.
- *A61K 35/17* (2015.01)
- *A61P 35/00* (2006.01)
- *C07K 14/725* (2006.01)
- *C07K 16/28* (2006.01)
- *A61K 38/00* (2006.01)

(52) U.S. Cl.
CPC .............. *A61K 35/17* (2013.01); *A61P 35/00* (2018.01); *C07K 14/7051* (2013.01); *C07K 16/2887* (2013.01); *A61K 38/00* (2013.01)

(58) Field of Classification Search
CPC ...................................................... A61K 37/17
See application file for complete search history.

(56) References Cited

U.S. PATENT DOCUMENTS

| | | | |
|---|---|---|---|
| 2017/0021811 A1* | 1/2017 | Norell | A47L 9/22 |
| 2017/0081411 A1* | 3/2017 | Engels | C07K 16/2803 |
| 2017/0159025 A1* | 6/2017 | Li | C07K 14/71 |
| 2017/0204177 A1* | 7/2017 | Wang | C12N 15/62 |
| 2018/0022795 A1* | 1/2018 | Milone | C07K 14/70535 435/328 |
| 2018/0371052 A1* | 12/2018 | Ma | A61K 35/17 |
| 2019/0038671 A1* | 2/2019 | Fan | C07K 16/2818 |
| 2019/0336534 A1* | 11/2019 | Stadheim | A61K 35/17 |
| 2020/0010803 A1* | 1/2020 | Adusumilli | C07K 14/70517 |
| 2021/0087279 A1* | 3/2021 | Engels | C07K 16/2803 |
| 2022/0001031 A1* | 1/2022 | Getts | C07K 14/7051 |

FOREIGN PATENT DOCUMENTS

| | | | | |
|---|---|---|---|---|
| CN | 106467906 B | 3/2017 | | |
| CN | 107384963 A | 11/2017 | | |
| WO | WO-2015188141 A2 * | 12/2015 | ............. | C07K 16/30 |
| WO | 2017028374 A1 | 2/2017 | | |
| WO | WO-2017112877 A1 * | 6/2017 | ............. | A61P 35/02 |

OTHER PUBLICATIONS

Nocentini et al. (Cell Death Differ. Apr. 2000; 7 (4): 408-10).*
Bridgeman et al. (J. Immunol. Jun. 15, 2010; 184 (12): 6938-49).*
Hudecek et al. (Clin. Cancer Res. Jun. 15, 2013; 19 (12): 3153-64).*
Boice et a. (Cell. Oct. 6, 2016; 167 (2): 405-18).*
Curran et al. (Mol. Ther. Apr. 2015; 23 (4): 769-78).*
Kim et al. (PLoS One. 2011; 6 (4): e18556; pp. 1-8).*
Martyniszyn et al. (Hum. Gene Ther. Dec. 2017; 28 (12): 1147-57).*
Morgan et al. (Biomedicines. Jun. 2016; 4 (2): 9; pp. 1-14).*
Hollyman et al. (J. Immunother. 2009; 32 (2): 169-80; author manuscript; pp. 1-22).*
Stephan et al. (Nat. Med. 2007; 13 (12): 1440-9).*
Zhao et al. (Cancer Cell. Oct. 12, 2015; 28 (4): 415-28; author manuscript; pp. 1-27).*
Drent et al. (Clin. Cancer Res. Jul. 1, 2019; 25 (13): 4014-25).*
Kuhn et al. (Cancer Cell. Mar. 18, 2019; 35 (3): 473-488).*
Zhong et al. (Mol. Ther. Feb. 2010; 18 (2): 413-20).*
Avanzi et al. (Cell Reports. 2018; 23: 2130-41).*
Vogler et al. (Mol. Ther. Jul. 2010; 18 (7): 1330-8).*
Chen et al. (Leukemia. 2018; 32: 402-12).*
Bielamowicz et al. (Neuro-Oncol. 2018; 20 (4): 506-18, 2018).*
Collinson-Pautz et al. (Leukemia. 2019; 33: 2195-207).*
Cherkassky et al. (J. Clin. Invest. 2016; 126 (8): 3130-3144).*
Perna et al. (Clin. Cancer Res. Jan. 1, 2014; 20 (1): 131-9).*
Pregram et al. (Blood. 2012; 119 (18): 4133-41).*
Di Stasi et al. (Blood. 2009; 113 (25): 6932-402).*
Subramanian et al. (Biotechnol. Biofuels. 2017; 10: 34; pp. 1-15).*
Wang et al. (Mol. Genet. Genomics. 2019; 294: 849-59).*
Brentjens et al. (Clin. Cancer Res. Sep. 15, 2007; 13 (18 Pt. 1): 5426-35).*
Dai et al. (Front. Immunol. Nov. 13, 2020; 11: 539654; pp. 1-11).*
Zhang et al. (Sci. Transl. Med. 2021; 13: eaba7308; pp. 1-17).*
Abate-Daga et al. (Mol. Ther. Oncolytics. May 18, 2016; 3: 16014; pp. 1-7).*

(Continued)

*Primary Examiner* — Stephen L Rawlings
(74) *Attorney, Agent, or Firm* — Honigman LLP; Thomas A. Wootton, Esq.; Jonathan P. O'Brien

(57) ABSTRACT

Provided by the present invention is a chimeric antigen receptor comprising a co-stimulatory receptor, the chimeric antigen receptor having a structure of scFv(X)-(Y)CD3zeta-2A-(Z); X comprises a tumortargeting antibody or a ligand or receptor capable of specifically binding to a tumor; Y is an intracellular region of the co-stimulatory receptor, and Z is a co-stimulatory receptor that is selected from among ICOS, CD28, CD27, HVEM, LIGHT, CD40L, 4-1BB, OX40, DR3, GITR, CD30, TIMI, SLAM, CD2, CD226. Further provided by the present invention are CAR-T cells that are constructed by means of a recombinant expression vector of the described chimeric antigen receptor, a preparation method therefor and an application thereof. The CAR-T cells described in the present invention significantly improve the tumor-killing abilities and amplification abilities thereof.

7 Claims, 11 Drawing Sheets

Specification includes a Sequence Listing.

(56) References Cited

OTHER PUBLICATIONS

Foster et al. (Mol. Ther. Sep. 6, 2017; 25 (9): 2176-88).*
Tang et al. (BMJ Open. 2016; 6 (12): e013904; electronically published Dec. 30, 216; pp. 1-7).*
Chang et al. (Trends Mol. Med. May 2017; 23 (5): 430-450; electronically published Apr. 13, 2017).*
Pegram et al. (Blood. May 3, 2012; 119 (18): 4133-41).*
Rafiq et al. (Nat. Biotechnol. Oct. 2018; 36 (9): 847-856).*
Weinkove et al. (Clin. Transl. Immunology. 2019; 8 (5): e1049; pp. 1-14).*
Finney et al. (J. Immunol. Jan. 1, 2004; 172 (1): 104-13).*
Song et al. (Immunity. May 2005; 22 (5): 621-31).*
PCT/CN2019/077922 International Search Report dated May 23, 2019.
Boice, M., et al., Loss of the HVEM Tumor Suppressor in Lymphoma and Restoration by Modified CAR-T Cells, Cell, vol. 167, Oct. 6, 2016.

* cited by examiner

CHIMERIC ANTIGEN RECEPTOR COMPRISING CO-STIMULATORY RECEPTOR AND APPLICATION THEREOF

CROSS-REFERENCE TO RELATED APPLICATIONS

This application is a Continuation of and claims priority under 35 U.S.C. § 111 to Patent Cooperation Treaty application PCT/CN2019/077922, filed Mar. 13, 2019, which claims the benefit of Chinese Patent Application No. 201810636409.0, filed Jun. 20, 2018, priority is claimed to both of these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "2020-12-18 262790-481980 ST25.txt" is 17,128 bytes in size and was created on Dec. 18, 2020, and filed electronically herewith.

TECHNICAL FIELD

The present invention relates to the field of cellular immunotherapeutic technology, especially relates to a chimeric antigen receptor comprising a co-stimulatory receptor and use thereof.

BACKGROUND OF THE INVENTION

The use of immunological therapy for overcoming tumors has always been an important direction in the application of immunology in translational medicine. With the development of various omics (genomics, proteomics, etc.), tumor cells have been widely recognized due to their immunogenicity caused by mutations, which lays a theoretical foundation for tumor immunotherapy. At the same time, with the accumulation of tumor immunology research itself, tumor immunotherapy has recently made a great progress, and a series of new immunotherapy methods have gradually entered into the clinic. The current tumor immunology research has established the central position of T cell killing in tumor immunotherapy, and the chimeric antigen receptor T cell (CAR-T cell) is a tumor-killing cell which has combined the targeted recognition of antibody and the tumor-killing function of T cell, and been generated by artificial modification.

The concept of chimeric antigen receptor T cell was first proposed by Gross, Waks and Eshhar in 1989. They expressed TNP-recognizing antibodies on T cells, achieving antigen-specific, non-MHC-restricted T cell activation and enhanced effect, and proposed the concept of the application of CAR-T technology in tumor treatment. According to this principle, tumor-specific antibodies are embedded into T cells, which will give T cells new tumor-killing capabilities. After that, CAR-T technology was introduced into anti-tumor clinical trials, but the final clinical results of early CAR-T cells are not ideal since their intracellular signal transmission domain contains only the first signal, and the selected tumor type is a solid tumor. In 2008, the Fred Hutchison Cancer Institute and other institutions used CAR-T to treat B cell lymphoma, although the treatment results are not ideal, the key to this clinical trial is to demonstrate that CAR-T treatment with CD20-expressing B cells as the target is relatively safe. Subsequently, in 2010, NCI reported a case of successful treatment of B-cell lymphoma, using CAR-T targeting CD19, the patient's lymphoma was controlled, normal B cells were also eliminated, and serum Ig was significantly reduced, providing a theoretical and practical support for the effectiveness of CAR-T in the treatment of B cell-derived lymphomas. In 2011, a team led by Dr. Carl June of the University of Pennsylvania in the United States used CAR-T that specifically recognizes CD19 for the treatment of chronic lymphocytic leukemia derived from B cells, showing a "cure" effect. After that, clinical trials have also been launched in relapsed and refractory acute lymphoblastic cell leukemia, and good results have also been achieved. Due to this breakthrough progress and the development of other immune regulation methods, Science magazine ranked tumor immunotherapy as the number one scientific and technological breakthrough in 2013. This success has caused widespread influence in countries around the world, and countries have begun to carry out a large number of CAR-T-based scientific research and clinical trials of tumor treatment.

The structure of CAR consists of an extracellular antigen recognition domain, an extracellular hinge region, a transmembrane domain, and an intracellular signal transduction domain. The extracellular antigen recognition domain generally consists of a single-chain antibody, which specifically recognizes membrane surface molecules of the tumor cell, or can be a ligand or receptor of certain tumor-specific antigens, etc. The extracellular hinge region is a spatial structure that separates the antigen recognition domain from the transmembrane domain, and its purpose is to provide a suitable spatial position, so that the extracellular antigen recognition domain can maintain the correct structure and transmit the intracellular signals before and after recognizing the antigen. The transmembrane domain is a domain for ensuring the positioning of the CAR molecule on the membrane surface. The intracellular signal transduction domain is a key part of mediating the CAR signal transduction, and is usually a combination of one or several first signals (for the recognition of TCR and MHC-I-peptide complex) and second signals (for the recognition of costimulatory receptor and costimulatory ligand). The first-generation CAR contains only the first signal, the second-generation CAR has one first signal and one second signal, and the third-generation CAR has one first signal and two second signal domains. Although CAR-T has achieved a great success in the treatment of leukemia derived from B cell, its relatively high recurrence rate and low effectiveness for solid tumors are important challenges currently. Therefore, there is an urgent clinic need of developing a new generation of high-efficiency CAR-T currently. In addition to the third-generation CAR-T, there are currently other new CAR-T design strategies, that is, new regulatory molecules independent of CAR are introduced on the basis of the second-generation CAR-T to further enhance the function of CAR-T.

The application of CAR-T targeting the B cell surface targeting molecules CD19 and CD20 prepared from the patient's own blood cells in the treatment of B cell leukemia has been relatively mature, but there are a large number of recurrences, even though the response rate is high. In addition, the treatment efficiency for solid lymphoma is relatively low, which is related to the immunosuppressive microenvironment in solid tumors.

In solid tumors, there are a variety of immune cells, tumor cells and stromal cells, which together constitute the tumor microenvironment. The tumor microenvironment is usually immunosuppressive, and can inhibit endogenous anti-tumor T cell responses or adoptive T cells (such as CAR-T) at multiple levels, for example, leading to exhaustion of T cells and loss of tumor killing function, and eventually leading to the clearance of T cells. How to enhance the activation ability of CAR-T in solid tumors so that CAR-T can fight against the immune suppression in the tumor microenvironment is an important idea and direction for expanding CAR-T to solid tumor treatment.

However, the current CAR-T domains in clinical use still have insufficient tumor killing and expansion abilities, and have poor efficacy in controlling solid tumors/metastasis. Some CAR-T use novel regulatory molecules such as IL-12, 4-1BBL, etc. These molecules will also produce non-specific activation effects on other non-CAR-T cells in addition to affecting the CAR-T, which may cause immune side effects.

SUMMARY OF THE INVENTION

An object of the present invention is to address the defects in the prior art, provide a chimeric antigen receptor including a co-stimulatory receptor and use thereof, and provide a CAR-T cell constructed by a recombinant expression vector of the chimeric antigen receptor. For example, OX40 is an important co-stimulatory receptor which is primarily expressed in activated CD4 and CD8 T cells, and displays a variety of functions during the activation of T cells. They can promote the activation of T cells, exhibit more effector molecules, and reduce the expression of gene associated with apoptosis. Integrating the co-stimulatory receptor signal into the CAR-T has a potential effect-enhancing function.

To address the aforesaid object, the present invention utilizes the following technical solutions:

a first object of the present invention is to provide a chimeric antigen receptor including a co-stimulatory receptor and having a structure of scFv(X)-(Y)CD3zeta-2A-(Z); wherein X is a tumor-targeting antibody or a ligand or receptor capable of specifically binding to a tumor; Y is an intracellular domain of a co-stimulatory receptor, and said co-stimulatory receptor is selected from ICOS, CD28, CD27, HVEM, LIGHT, CD40L, 4-1BB, OX40, DR3, GITR, CD30, TIM1, SLAM, CD2, CD226; Z is a co-stimulatory receptor, and said co-stimulatory receptor is selected from ICOS, CD28, CD27, HVEM, LIGHT, CD40L, 4-1BB, OX40, DR3, GITR, CD30, TIM1, SLAM, CD2, CD226.

For further optimizing the aforesaid chimeric antigen receptor, the technical means used in the present invention further includes:

Further, the X is selected from anti-CD19 antibody, anti-CD20 antibody, EGFR antibody, HER2 antibody, EGFRVIII antibody, anti-PSMA antibody, anti-BCMA antibody, anti-CD22 antibody, anti-CD30 antibody. Understandably, X can also be other protein capable of specifically binding to a tumor.

Further, said X is anti-CD20 antibody, said Y is 4-1BB, said Z is one selected from OX40, HVEM, ICOS, CD27, 4-1BB.

Further, said scFv(X)-(Y)CD3zeta is scFv-antihCD20-20BBZ having a sequence of SEQ ID No. 1; said OX40 has a sequence of SEQ ID No.2; said HVEM has a sequence of SEQ ID No.3; said ICOS has a sequence of SEQ ID No.4; said CD27 has a sequence of SEQ ID No.5; said 4-1BB has a sequence of SEQ ID No.6; and said 2A has a sequence of SEQ ID No.7, SEQ ID No.8, SEQ ID No.9 or SEQ ID No.10.

Wherein the aforesaid sequences are as follows:

SEQ ID No. 1:
QIVLSQSPAILSASPGEKVTMTCRASSSVSYIHWFQQKPGSSPKPWIYATS
NLASGVPVRFSGSGSGTSYSLTISRVEAEDAATYYCQQWTSNPPTFGGGTK
LEIKGGGGSGGGGSGGGGSQVQLQQPGAELVKPGASVKMSCKASGYTFTSY
NMHWVKQTPGRGLEWIGAIYPGNGDTSYNQKFKGKATLTADKSSSTAYMQL
SSLTSEDSAVYYCARSTYYGGDWYFNVWGAGTTVTVSAAAATTTPAPRPPT
PAPTIASQPLSLRPEACRPAAGGAVHTRGLDFACDIYIWAPLAGTCGVLLL
SLVITLYCKRGRKKLLYIFKQPFMRPVQTTQEEDGCSCRFPEEEEGGCELR
VKFSRSADAPAYQQGQNQLYNELNLGRREEYDVLDKRRGRDPEMGGKPRRK
NPQEGLYNELQKDKMAEAYSEIGMKGERRRGKGHDGLYQGLSTATKDTYDA
LHMQALPPR;

SEQ ID No. 2:
MCVGARRLGRGPCAALLLLGLGLSTVTGLHCVGDTYPSNDRCCHECRPGNG
MVSRCSRSQNTVCRPCGPGFYNDVVSSKPCKPCTWCNLRSGSERKQLCTAT
QDTVCRCRAGTQPLDSYKPGVDCAPCPPGHFSPGDNQACKPWTNCTLAGKH
TLQPASNSSDAICEDRDPPATQPQETQGPPARPITVQPTEAWPRTSQGPST
RPVEVPGGRAVAAILGLGLVLGLLGPLAILLALYLLRRDQRLPPDAHKPPG
GGSFRTPIQEEQADAHSTLAKI;

SEQ ID No. 3:
MEPPGDWGPPPWRSTPKTDVLRLVLYLTFLGAPCYAPALPSCKEDEYPVGS
ECCPKCSPGYRVKEACGELTGTVCEPCPPGTYIAHLNGLSKCLQCQMCDPA
MGLRASRNCSRTENAVCGCSPGHFCIVQDGDHCAACRAYATSSPGQRVQKG
GTESQDTLCQNCPPGTFSPNGTLEECQHQTKCSWLVTKAGAGTSSSHWVWW
FLSGSLVIVIVCSTVGLIICVKRRKPRGDVVKVIVSVQRKRQEAEGEATVI
EALQAPPDVTTVAVEETIPSFTGRSPNH;

SEQ ID No. 4:
MKSGLWYFFLFCLRIKVLTGEINGSANYEMFIFHNGGVQILCKYPDIVQQF
KMQLLKGGQILCDLTKTKGSGNTVSIKSLKFCHSQLSNNSVSFFLYNLDHS
HANYYFCNLSIFDPPPFKVTLTGGYLHIYESQLCCQLKFWLPIGCAAFVVV
CILGCILICWLTKKKYSSSVHDPNGEYMFMRAVNTAKKSRLTDVTL;

SEQ ID No. 5:
MARPHPWWLCVLGTLVGLSATPAPKSCPERHYWAQGKLCCQMCEPGTFLVK
DCDQHRKAAQCDPCIPGVSFSPDHHTRPHCESCRHCNSGLLVRNCTITANA
ECACRNGWQCRDKECTECDPLPNPSLTARSSQALSPHPQPTHLPYVSEMLE
ARTAGHMQTLADFRQLPARTLSTHWPPQRSLCSSDFIRILVIFSGMFLVFT
LAGALFLHQRRKYRSNKGESPVEPAEPCRYSCPREEEGSTIPIQEDYRKPE
PACSP;

SEQ ID No. 6:
MGNSCYNIVATLLLVLNFERTRSLQDPCSNCPAGTFCDNNRNQICSPCPPN
SFSSAGGQRTCDICRQCKGVFRTRKECSSTSNAECDCTPGFHCLGAGCSMC
EQDCKQGQELTKKGCKDCCFGTFNDQKRGICRPWTNCSLDGKSVLVNGTKE

-continued
RDVVCGPSPADLSPGASSVTPPAPAREPGHSPQIISFFLALTSTALLFLLF

FLTLRFSVVKRGRKKLLYIFKQPFMRPVQTTQEEDGCSCRFPEEEEGGCE

L;

SEQ ID No. 7:
GSGATNFSLLKQAGDVEENPGP;

SEQ ID No. 8:
GSGEGRGSLLTCGDVEENPGP;

SEQ ID No. 9:
GSGQCTNYALLKLAGDVESNPGP;

SEQ ID No. 10:
GSGVKQTLNFDLLKLAGDVESNPGP.

Further, the extracellular hinge region of said chimeric antigen receptor is a region selected from CD8a or IgG; and the transmembrane domain of said chimeric antigen receptor is one selected from CD8a, CD28, CD137 or CD3.

A second object of the present invention is to provide a recombinant expression vector of any one of the aforesaid chimeric antigen receptors.

A third object of the present invention is to provide a CAR-T cell constructed by a recombinant expression vector of any one of the aforesaid chimeric antigen receptors.

A fourth object of the present invention is to provide a method of preparing the aforesaid CAR-T cell which includes the following steps:

step 1: construction of lentiviral vector and production of virus;

incorporating 2A between scFv(X)-(Y)CD3zeta and Z to form a fusion protein, adding a lentiviral vector to both ends of the fusion protein, and co-transfecting with lentiviral packaging plasmid to obtain an scFv(X)-(Y)CD3zeta-2A-(Z) virus;

step 2, preparation of scFv(X)-(Y)CD3zeta-2A-(Z) CAR-T cell;

culturing purified human PBMC and infecting said PBMC with the scFv(X)-(Y)CD3zeta-2A-(Z) virus obtained in Step 1, and subjecting them to cell expansion under suitable conditions to prepare scFv(X)-(Y)CD3zeta-2A-(Z) CAR-T cell.

For further optimizing the method of preparing the aforesaid CAR-T cell, the technical means used in the present invention further includes:

Further, said construction of lentiviral vector and production of virus include: incorporating 2A between scFv(X)-(Y)CD3zeta and Z by overlap PCR to form a fusion protein, and adding restriction sites to both ends of the fusion protein to clone a lentiviral vector; subjecting the clones sequenced correctly to a large scale endotoxin-free extraction, and co-transfecting with lentiviral packaging plasmid, after a predetermined period of time, collecting a supernatant, filtering, centrifuging to concentrate the virus to obtain an scFv(X)-(Y)CD3zeta-2A-(Z) virus.

Still further, the specific steps of the construction of lentiviral vector and production of virus are as follows: incorporating 2A sequence between scFv(X)-(Y)CD3zeta and OX40 by overlap PCR, adding EcoRI and SalI restriction sites to both ends of the fusion protein to clone the pCDH-MSCVEF vector, subjecting the clones sequenced correctly to a large scale endotoxin-free extraction, and co-transfecting with lentiviral packaging plasmid into 293X; after 48 and 72 hours, collecting the supernatant, filtering it by a 0.45 uM filter and performing centrifugation at 25000RPM for 2 hours to concentrate the viruses to obtain the scFv(X)-(Y)CD3zeta-2A-(Z) virus.

Further, the specific steps of the preparation of scFv(X)-(Y)CD3zeta-2A-(Z) CAR-T cell include: isolating human PBMC for purification, inoculating into a culture plate under suitable stimulation conditions, culturing for a predetermined period of time, infecting said PBMC with the scFv(X)-(Y)CD3zeta-2A-(Z) virus obtained in Step 1, and subjecting it to cell expansion under suitable stimulation conditions, after 2 rounds of expansion under stimulation, the obtained cells are the scFv(X)-(Y)CD3zeta-2A-(Z) CAR-T cells.

Further, the stimulation conditions for culturing the isolated and purified human PBMC are anti-hCD3 and anti-hCD28; and the stimulation conditions for cell expansion are stimulation by use of artificial antigen presenting cell or anti-hCD3/28 every 6 days.

Still further, the specific steps of preparing the scFv(X)-(Y)CD3zeta-2A-(Z) CAR-T cell are as follows: purifying human PBMC by a Stemcell T cell isolation kit, inoculating into a 96-well culture plate coated by anti-hCD3 and anti-hCD28. After 2 days, infecting the cells with the scFv(X)-(Y)CD3zeta-2A-(Z) virus at MOI=10-20. After 1 day, continuing to culture the cells with the medium changed, and stimulating them by artificial antigen presenting cell or anti-hCD3/28 every 6 days. After 2 rounds of stimulation, the obtained cells are scFv(X)-(Y)CD3zeta-2A-(Z) CAR-T cells.

Further, said X is selected anti-CD19 antibody, anti-CD20 antibody, EGFR antibody, HER2 antibody, EGFRVIII antibody.

Further, said X is anti-CD20 antibody, said Y is 4-1BB, said Z is one selected from OX40, HVEM, ICOS, CD27, 4-1BB.

Further, said scFv(X)-(Y)CD3zeta is scFv-antihCD20-20BBZ having a sequence of SEQ ID No. 1; said OX40 has a sequence of SEQ ID No.2; said HVEM has a sequence of SEQ ID No.3; said ICOS has a sequence of SEQ ID No.4; said CD27 has a sequence of SEQ ID No.5; said 4-1BB has a sequence of SEQ ID No.6; and said 2A has a sequence of SEQ ID No.7.

Further, the lentiviral packaging plasmid in Step 1 includes VSV-g, pMD Gag/Pol, RSV-REV, and the centrifugation is performed with Beckman ultracentrifuge and SW28 head.

A fifth object of the present invention is to provide a formulation including the aforesaid CAR-T cell or the CAR-T cell prepared by the aforesaid preparation method. Further, the formulation also includes a pharmaceutically diluents or excipient.

A sixth object of the present invention is to provide a use of the aforesaid chimeric antigen receptor, the aforesaid CAR-T cell or the CAR-T cell prepared by the aforesaid preparation method in preparation of a medicament for treating or preventing tumor.

Further, said tumors are solid tumors. Examples of said solid tumors include, but are not limited to, lymphomas, renal tumors, neuroblastoma, germ cell tumor, osteosarcoma, chondrosarcoma, soft tissue sarcoma, liver tumor, thymoma, pulmonary blastoma, pancreatoblastoma, hemangioma, etc.

As compared with the prior art, the present invention has the following beneficial effects:

the CAR-T cell of the present invention significantly increases the tumor killing ability and expansion ability, and exhibits a greatly increased solid/metastasis tumor killing ability. The CAR-T cell of the present invention includes a co-stimulatory receptor (ICOS, CD28, CD27, HVEM, LIGHT, CD40L, 4-1BB, OX40, DR3, GITR, CD30, TIM1, SLAM, CD2, CD226, etc.), instead of a conventionally used ligand or excreted factor, and works only on the CAR-T cell, thereby reducing the risk of causing an immune side effect.

The present invention first utilizes the co-stimulatory receptor in the construction of CAR-T. As compared with the current CAR-T technology in clinic use, the present invention significantly increases the activation ability and survival ability of CAR-T cell in tumors, and controls the ability of solid/metastatic tumors, thereby improving the therapeutic effect of the CAR-T cell to get a more superior anti-tumor therapeutic effect.

DETAILED DESCRIPTION OF THE INVENTION

The present invention provides a chimeric antigen receptor including a co-stimulatory receptor having a structure of scFv(X)-(Y)CD3zeta-2A-(Z); wherein X is a tumor-targeting antibody or other protein; Y is an intracellular domain of a co-stimulatory receptor, and said co-stimulatory receptor is selected from ICOS, CD28, CD27, HVEM, LIGHT, CD40L, 4-1BB, OX40, DR3, GITR, CD30, TIM1, SLAM, CD2, CD226; Z is a co-stimulatory receptor, and said co-stimulatory receptor is selected from ICOS, CD28, CD27, HVEM, LIGHT, CD40L, 4-1BB, OX40, DR3, GITR, CD30, TIM1, SLAM, CD2, CD226. The present invention also relates to a CAR-T cell constructed by a recombinant expression vector of any one of the aforesaid chimeric antigen receptor and a preparation method therefor, a formulation including the CAR-T cell, and a use of the CAR-T cell.

Hereinafter the embodiments of the present invention are further described with reference to the accompanying drawings and examples. The following examples are only for more clearly illustrating the technical solutions of the present invention, but not for limiting the protective scope of the present invention.

Figure 1:
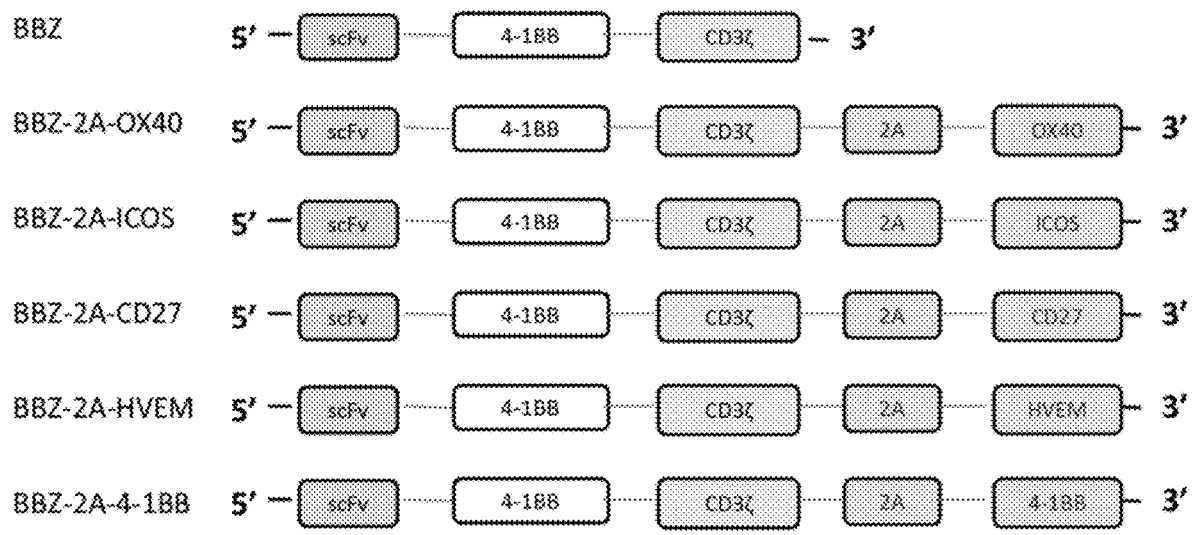
FIG. 1 is an illustrative schematic view showing the molecular structure of chimeric antigen receptor (CAR) including the third signal receptor in embodiments of the present invention.

The chimeric antigen receptor (CAR) molecules including a co-stimulatory receptor used in the following examples of the present invention are BBZ-2A-OX40, BBZ-2A-HVEM, BBZ-2A-ICOS, BBZ-2A-CD27, BBZ-2A-4-1BB, respectively, and their structures are shown in FIG. 1.

Example 1—Preparation of 20BBZ-2A-OX40 CAR-T Cell

Figure 2:
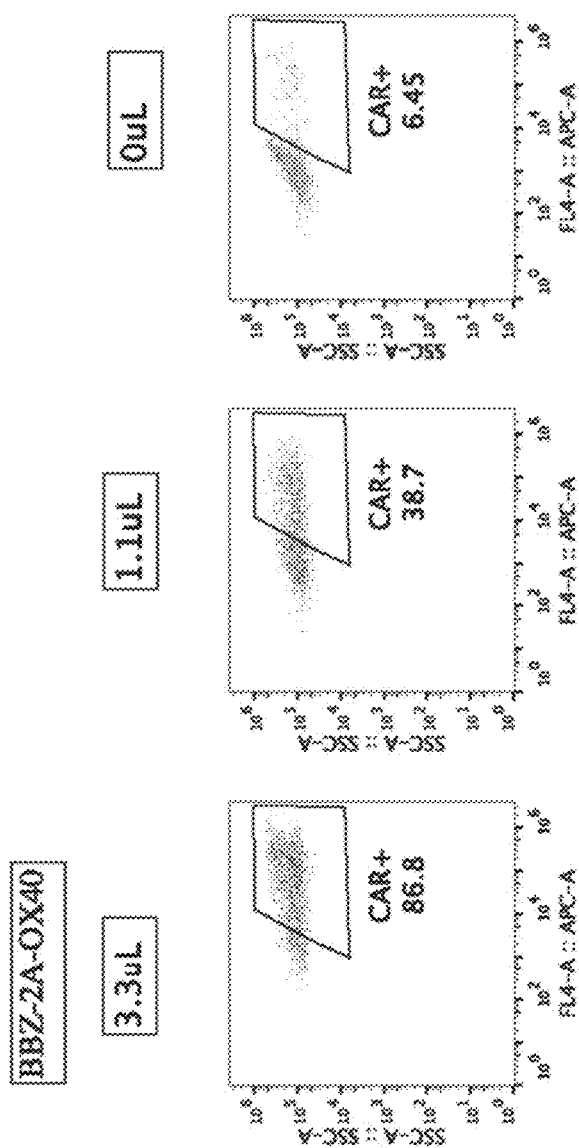
FIG. 2 is a schematic view showing the virus titer measured after 293 cells were infected with BBZ-2A-OX40 virus in an embodiment of the present invention.

The preparation of the 20BBZ-2A-OX40 CAR-T cell in this example includes the following steps:

1. Construction of Lentiviral Vector pCDH-MSCVEF-20BBZ-2A-OX40 and Production of Virus incorporating 2A (SEQ ID No. 7) sequence between scFv-antihCD20-20BBZ (SEQ ID No.1) and OX40 (SEQ ID No.2) by overlap PCR, and adding EcoRI and SalI restriction sites to both ends to clone the pCDH-MSCVEF vector. Subjecting the clones sequenced correctly to a large scale endotoxin-free extraction, and co-transfecting with lentiviral packaging plasmid (VSV-g, pMD Gag/Pol, RSV-REV) into 293X. After 48 and 72 hours, collecting the supernatant, filtering it by a 0.45 uM filter, and performing centrifugation with Beckman ultracentrifuge and SW28 head at 25000 RPM for 2 hours to concentrate the virus, which is pCDH-MSCVEF-20BBZ-2A-OX40 virus (briefly, 20BBZ-2A-OX40 virus) for the subsequent production of CAR-T cell. Meanwhile, producing the control pCDH-MSCVEF-20BBZ virus (briefly, 20BBZ virus), and infecting 293 cells with the obtained virus to measure the virus titer, as shown in FIG. 2.

Figure 7:
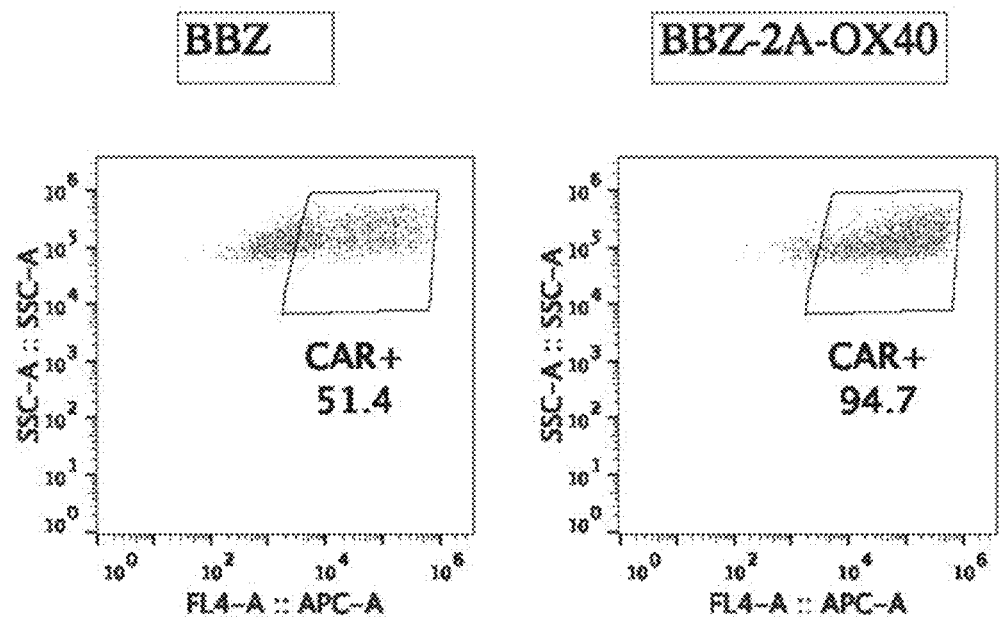
FIG. 7 is a schematic view showing the results of phenotypic analysis of BBZ CAR-T cell and BBZ-2A-OX40 CAR-T cell in an embodiment of the present invention.

2. Preparation of 20BBZ-2A-OX40 CAR-T Cell and 20BBZ CAR-T Cell purifying human PBMC by a Stemcell T cell isolation kit, and inoculating into a 96-well culture plate coated with anti-hCD3 and anti-hCD28. After 2 days, infecting the cells with 20BBZ virus and 20BBZ-2A-OX40 virus at MOI=10-20. After 1 day, continuing to culture the cells with the medium changed, and stimulating them by artificial antigen presenting cell or anti-hCD3/28 every 6 days. After 2 rounds of stimulation, the obtained cells are 20BBZCAR-T cell and 20BBZ-2A-OX40 CAR-T cell for subsequent experiments and phenotypic analysis. The results are shown in FIG. 7. It can be seen that the obtained cells are CAR-POSITIVE.

Example 2—Preparation of 20BBZ-2A-HVEM CAR-T Cell

Figure 3:
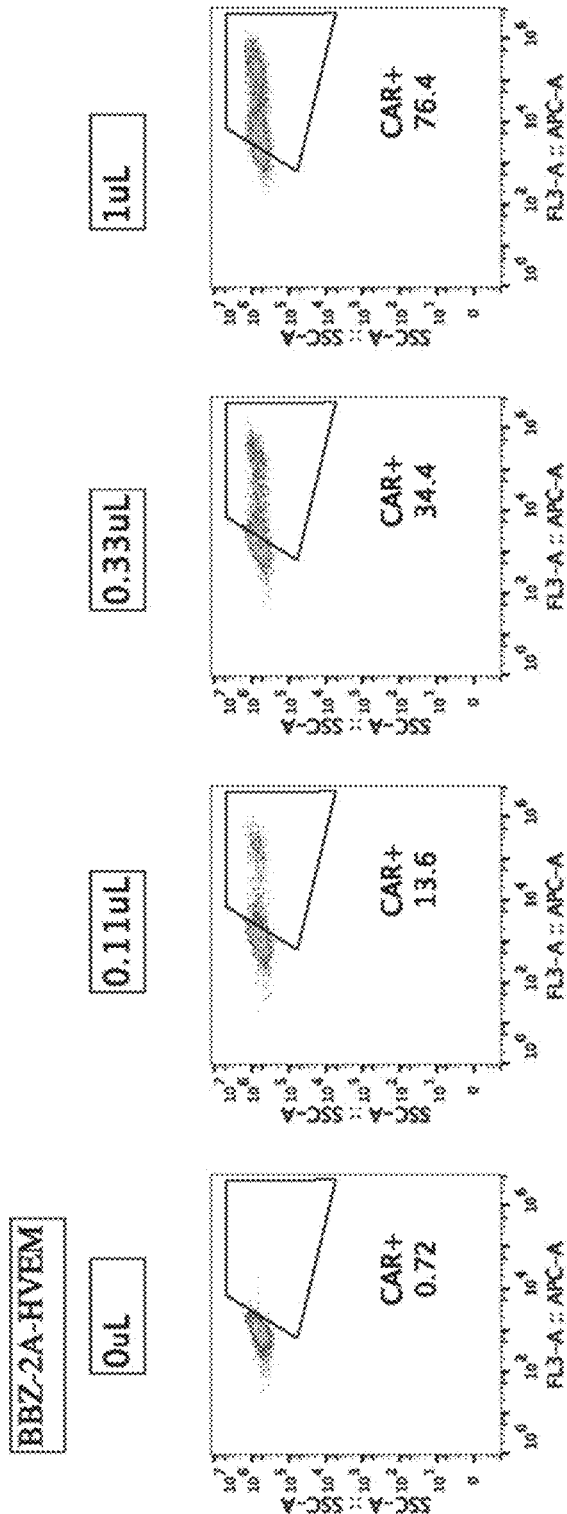
FIG. 3 is a schematic view showing the virus titer measured after 293 cells were infected with BBZ-2A-HVEM virus in an embodiment of the present invention.

The preparation of the 20BBZ-2A-HVEM CAR-T cell in in this example includes the following steps:

1. Construction of Lentiviral Vector pCDH-MSCVEF-20BBZ-2A-HVEM and Production of Virus incorporating 2A (SEQ ID No. 8) sequence between scFv-antihCD20-20BBZ (SEQ ID No.1) and HVEM (SEQ ID No.3) by overlap PCR, and adding EcoRI and SalI restriction sites to both ends to clone pCDH-MSCVEF vector. Subjecting the clones sequenced correctly to a large scale endotoxin-free extraction, and co-transfecting with lentiviral packaging plasmid (VSV-g, pMD Gag/Pol, RSV-REV) into 293X. After 48 and 72 hours, collecting the supernatant, filtering it by a 0.45 uM filter, and performing centrifugation with Beckman ultracentrifuge and SW28 head at 25000 RPM for 2 hours to concentrate the virus, which is pCDH-MSCVEF-20BBZ-2A-HVEM virus (briefly, 20BBZ-2A-HVEM virus) for the subsequent production of CAR-T cell. Meanwhile, producing the control pCDH-MSCVEF-20BBZ virus (briefly, 20BBZ virus). Infecting 293 cells with the obtained virus to measure the virus titer, as shown in FIG. 3.

Figure 8:
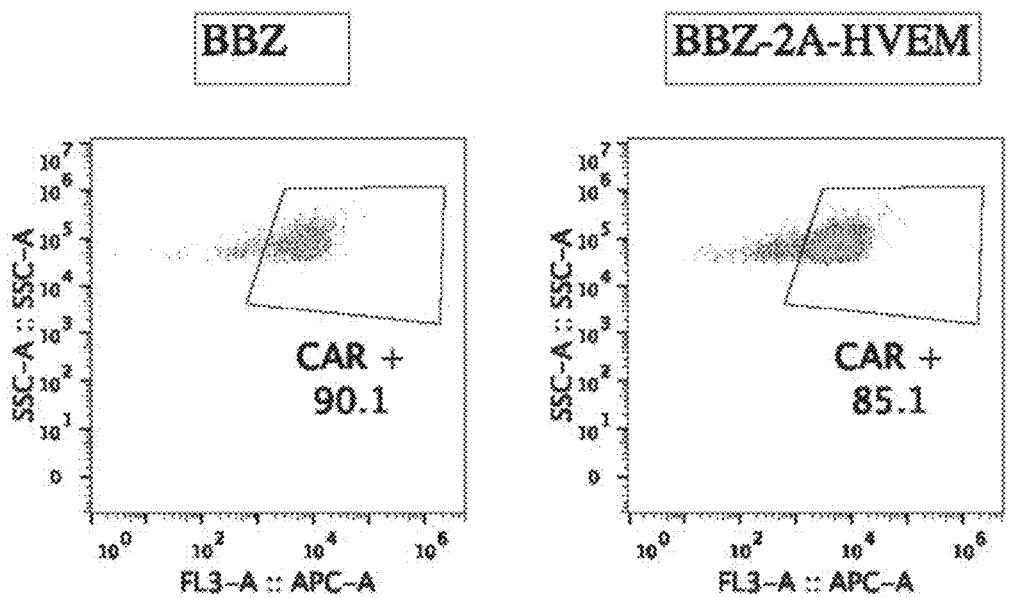
FIG. 8 is a schematic view showing the results of phenotypic analysis of BBZ CAR-T cell and BBZ-2A-HVEM CAR-T cell in an embodiment of the present invention.

2. Preparation of 20BBZ-2A-HVEM CAR-T Cell and 20BBZ CAR-T Cell purifying human PBMC by a Stemcell T cell isolation kit, and inoculating into a 96-well culture plate coated with anti-hCD3 and anti-hCD28. After 2 days, infecting the cells were infecte with 20BBZ virus and 20BBZ-2A-HVEM virus at MOI=10-20. After 1 day, continuing to culture the cells with the medium changed, and stimulating them by artificial antigen presenting cell or anti-hCD3/28 every 6 days. After 2 rounds of stimulation, the obtained cells are 20BBZCAR-T cell and 20BBZ-2A-HVEM CAR-T cell for subsequent experiments and phenotypic analysis. The results are shown in FIG. 8. It can be seen from the figure that the obtained cells are CAR-POSITIVE.

Example 3—Preparation of 20BBZ-2A-ICOS CAR-T Cell

Figure 4:
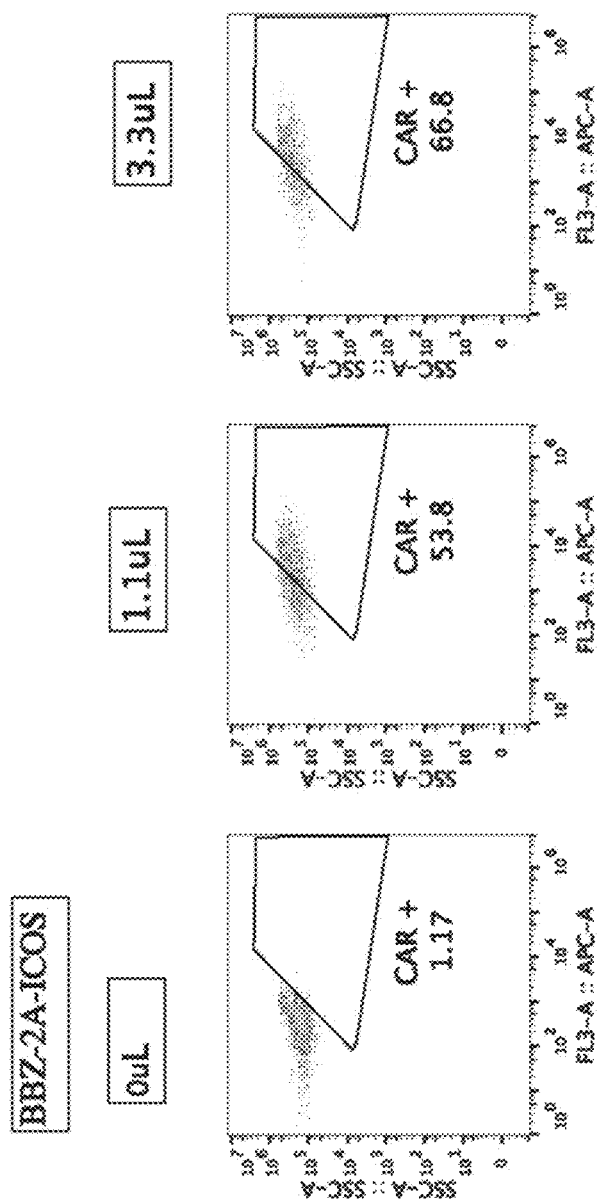
FIG. 4 is a schematic view showing the virus titer measured after 293 cells were infected with BBZ-2A-ICOS virus in an embodiment of the present invention.

The preparation of the 20BBZ-2A-ICOS CAR-T cell in this example includes the following steps:

1. Construction of Lentiviral Vector pCDH-MSCVEF-20BBZ-2A-ICOS and Production of Virus incorporating 2A (SEQ ID No. 9) sequence between scFv-antihCD20-20BBZ (SEQ ID No.1) and ICOS (SEQ ID No.4) by overlap PCR, and adding EcoRI and SalI restriction sites to both ends to clone pCDH-MSCVEF vector. Subjecting the clones sequenced correctly to a large scale endotoxin-free extraction, and co-transfecting with lentiviral packaging plasmid (VSV-g, pMD Gag/Pol, RSV-REV) into 293X. After 48 and 72 hours, collecting the supernatant, filtering it by a 0.45 uM filter, and performing centrifugation with Beckman ultracentrifuge and SW28 head at 25000 RPM for 2 hours to concentrate the virus, which is pCDH-MSCVEF-20BBZ-2A-ICOS virus (briefly, 20BBZ-2A-ICOS virus) for the subsequent production of CAR-T cell. Meanwhile, producing the control pCDH-MSCVEF-20BBZ virus (briefly, 20BBZ virus), and infecting 293 cells with the obtained virus to measure the virus titer, as shown in FIG. 4.

Figure 9:
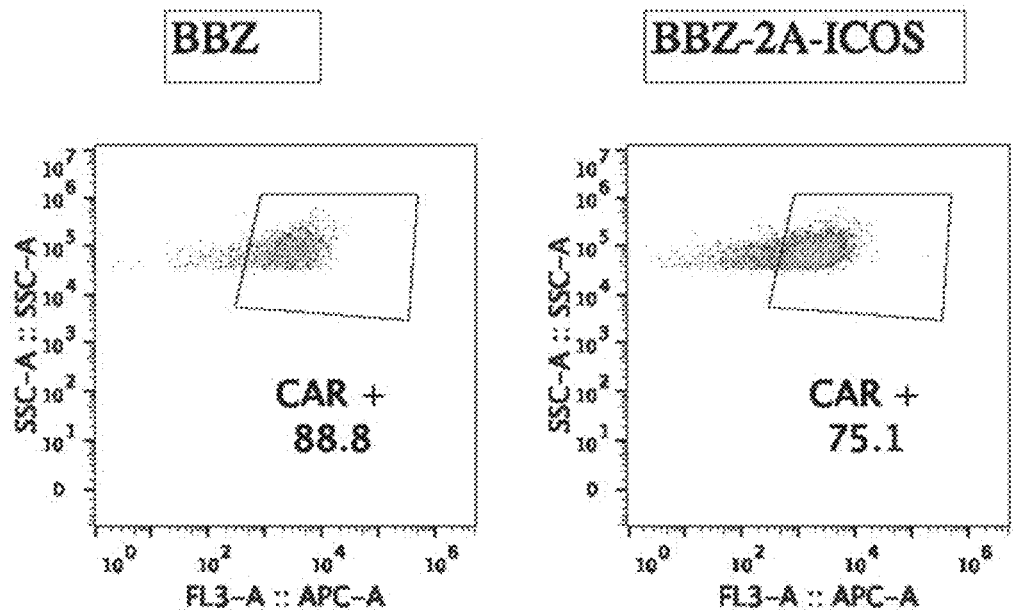
FIG. 9 is a schematic view showing the results of phenotypic analysis of BBZ CAR-T cell and BBZ-2A-ICOS CAR-T cell in an embodiment of the present invention.

2. Preparation of 20BBZ-2A-ICOS CAR-T Cell and 20BBZ CAR-T Cell purifying human PBMCs by a Stemcell T cell isolation kit, and inoculating into a 96-well culture plate coated with anti-hCD3 and anti-hCD28. After 2 days, infecting the cells with 20BBZ virus and 20BBZ-2A-ICOS virus at MOI=10-20. After 1 day, continuing to culture the cells with the medium changed, and stimulating them by artificial antigen presenting cell or anti-hCD3/28 every 6 days. After 2 rounds of stimulation, the obtained cells are 20BBZCAR-T cell and 20BBZ-2A-ICOS CAR-T cell for subsequent experiments and phenotypic analysis. The results are shown in FIG. 9. It can be seen from the figure that the obtained cells are CAR-POSITIVE.

Example 4—Preparation of 20BBZ-2A-CD27 CAR-T Cell

Figure 5:
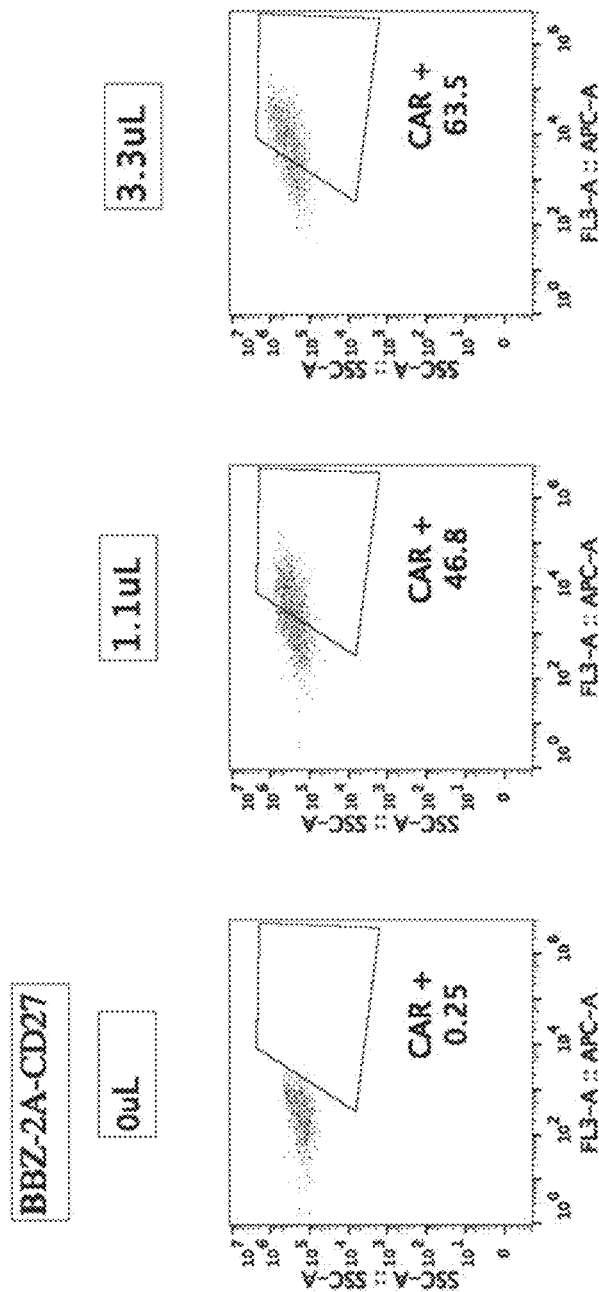
FIG. 5 is a schematic view showing the virus titer measured after 293 cells were infected with BBZ-2A-CD27 virus in an embodiment of the present invention.

The preparation of 20BBZ-2A-CD27 CAR-T cell in this example includes the following steps:

1. Construction of Lentiviral Vector pCDH-MSCVEF-20BBZ-2A-CD27 and Production of Virus incorporating 2A (SEQ ID No. 10) sequence between scFv-antihCD20-20BBZ (SEQ ID No.1) and CD27 (SEQ ID No.5) by overlap PCR, and adding EcoRI and SalI restriction sites to both ends to clone pCDH-MSCVEF vector. Subjecting the clones sequenced correctly to a large scale endotoxin-free extraction, and co-transfecting with lentiviral packaging plasmid (VSV-g, pMD Gag/Pol, RSV-REV) into 293X. After 48 and 72 hours, collecting the supernatant, filtering it by a 0.45 uM filter, and performing centrifugation with Beckman ultracentrifuge and SW28 head at 25000 RPM for 2 hours to concentrate the virus, which is pCDH-MSCVEF-20BBZ-2A-CD27 virus (briefly, 20BBZ-2A-CD27 virus) for the subsequent production of CAR-T cell. Meanwhile, producing the control pCDH-MSCVEF-20BBZ virus (briefly, 20BBZ virus), and infecting 293 cells with the obtained virus to measure the virus titer, as shown in FIG. 5.

Figure 10:
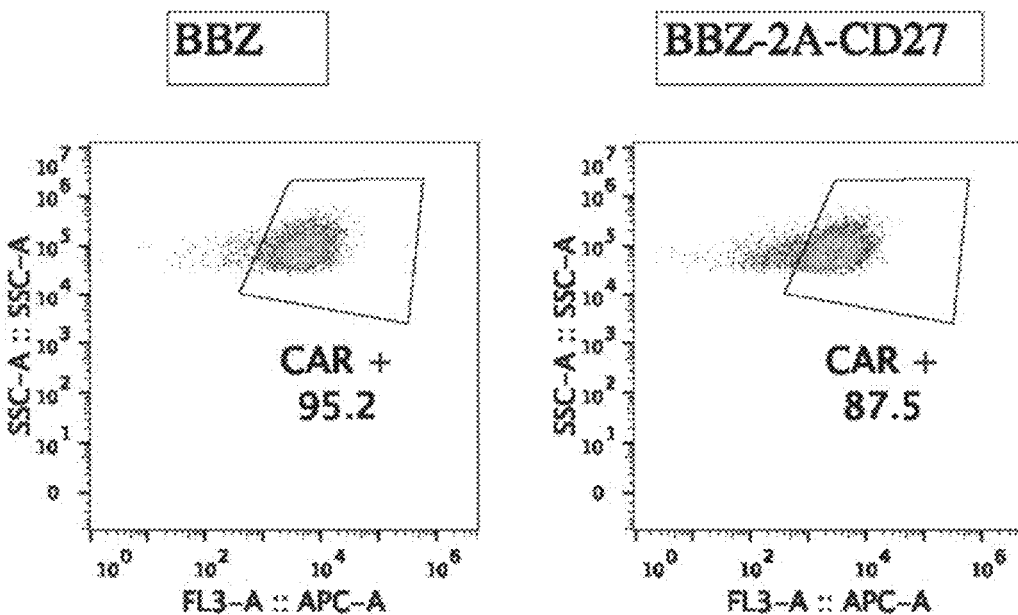
FIG. 10 is a schematic view showing the results of phenotypic analysis of BBZ CAR-T cell and BBZ-2A-CD27 CAR-T cell in an embodiment of the present invention.

2. Preparation of 20BBZ-2A-CD27 CAR-T Cell and 20BBZ CAR-T Cell purifying human PBMC by a Stemcell T cell isolation kit, and inoculating into a 96-well culture plate coated with anti-hCD3 and anti-hCD28. After 2 days, infecting the cells with 20BBZ virus and 20BBZ-2A-CD27 virus at MOI=10-20. After 1 day, continuing to culture the cells with the medium changed, and stimulating them by artificial antigen presenting cell or anti-hCD3/28 every 6 days. After 2 rounds of stimulation, the obtained cells are 20BBZCAR-T cell and 20BBZ-2A-CD27 CAR-T cell for subsequent experiments and phenotypic analysis. The results are shown in FIG. 10. It can be seen from the figure that the obtained cells are CAR-POSITIVE.

Example 5—Preparation of 20BBZ-2A-4-1BB CAR-T Cell

Figure 6:
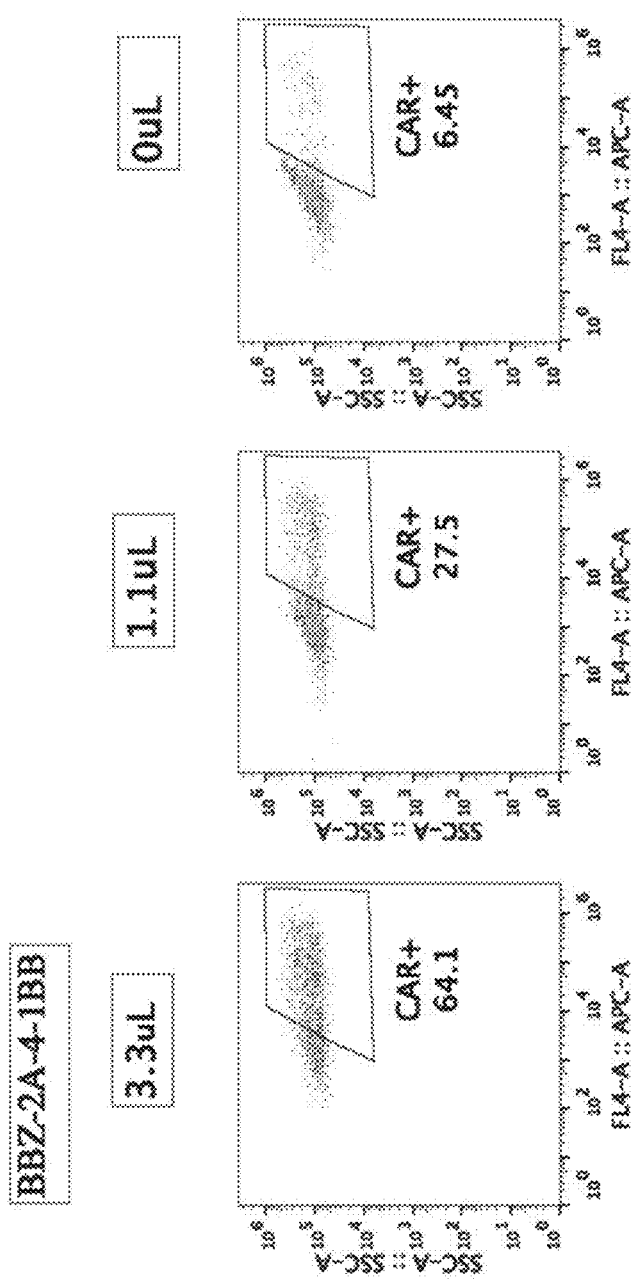
FIG. 6 is a schematic view showing the virus titer measured after 293 cells were infected with BBZ-2A-4-1BB virus in an embodiment of the present invention.

The preparation of the 20BBZ-2A-4-1BB CAR-T cell in this example includes the following steps:

1. Construction of Lentiviral Vector pCDH-MSCVEF-20BBZ-2A-4-1BB and Production of Virus incorporating 2A (SEQ ID No. 7) sequence between scFv-antihCD20-20BBZ (SEQ ID No.1) and 4-1BB (SEQ ID No.6) by overlap PCR, and adding EcoRI and SalI restriction sites to both ends to clone pCDH-MSCVEF vector. Subjecting the clones sequenced correctly to a large scale endotoxin-free extraction, and co-transfecting with lentiviral packaging plasmid (VSV-g, pMD Gag/Pol, RSV-REV) into 293X. After 48 and 72 hours, collecting the supernatant, filtering it by a 0.45 uM filter, and performing centrifugation with Beckman ultracentrifuge and SW28 head at 25000 RPM for 2 hours to concentrate the virus, which is pCDH-MSCVEF-20BBZ-2A-4-1BB virus (briefly, 20BBZ-2A-4-1BB virus) for the subsequent production of CAR-T cell. Meanwhile, producing the control pCDH-MSCVEF-20BBZ virus (briefly, 20BBZ virus), infecting 293 cells with the obtained virus to measure the virus titer, as shown in FIG. 6.

Figure 11:
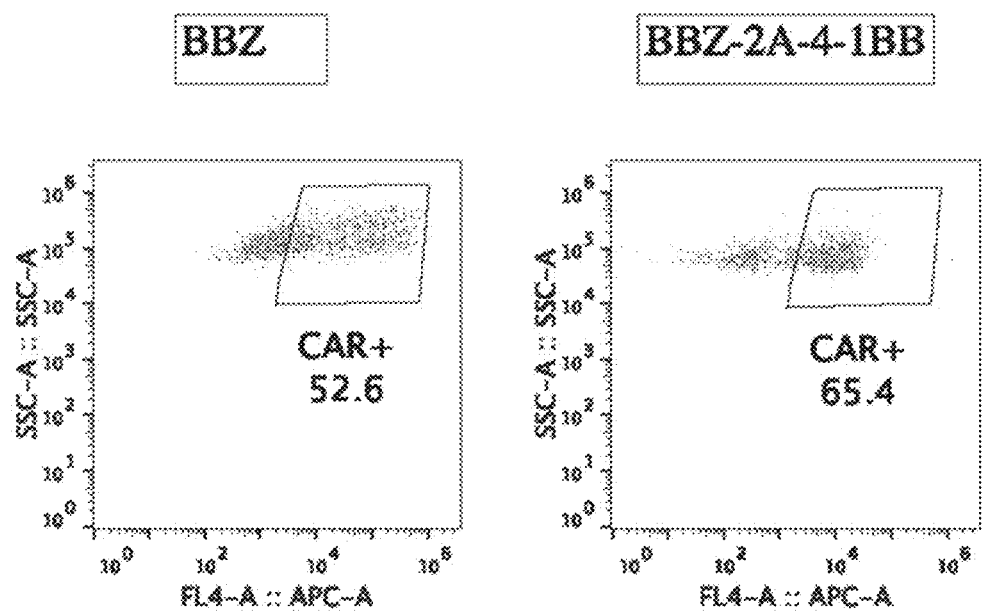
FIG. 11 is a schematic view showing the results of phenotypic analysis of BBZ CAR-T cell and BBZ-2A-4-1BB CAR-T cell in an embodiment of the present invention.

2. Preparation of 20BBZ-2A-4-1BB CAR-T Cell and 20BBZ CAR-T Cell purifying human PBMC by a Stemcell T cell isolation kit, and inoculating into a 96-well culture plate coated with anti-hCD3 and anti-hCD28. After 2 days, infecting the cells with 20BBZ virus and 20BBZ-2A-4-1BB virus at MOI=10-20. After 1 day, continuing to culture the cells with the medium changed, and stimulating them by artificial antigen presenting cell or anti-hCD3/28 every 6 days. After 2 rounds of stimulation, the obtained cells are 20BBZCAR-T cell and 20BBZ-2A-4-1BB CAR-T cell for subsequent experiments and phenotypic analysis. The results are shown in FIG. 11. It can be seen from the figure that the obtained cells are CAR-POSITIVE.

Figure 12:
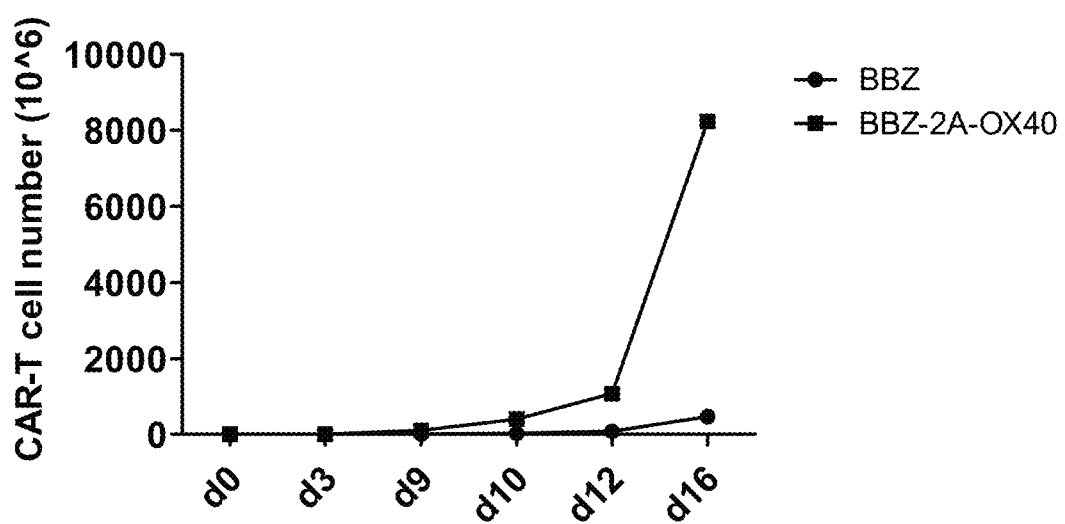
FIG. 12 is a schematic view showing the expansion ability of BBZ CAR-T cell and BBZ-2A-OX40 CAR-T cell in an embodiment of the present invention.

Example 6—Comparison of Expansion Abilities of 20BBZ CAR-T Cell and 20BBZ-2A-OX40 CAR-T Cell 20BBZ CAR-T cell and 20BBZ-2A-OX40 CAR-T cell prepared in Step 2 of Example 1 were continuously cultured for 14 days, and stimulated with artificial antigen presenting cell once every 6 days. The cells were counted, and the results are shown in FIG. 12. It can be seen from the figure that 20BBZ-2A-OX40 CAR-T cell has enhanced proliferation ability as compared with 20BBZCAR-T cell.

Figure 13:
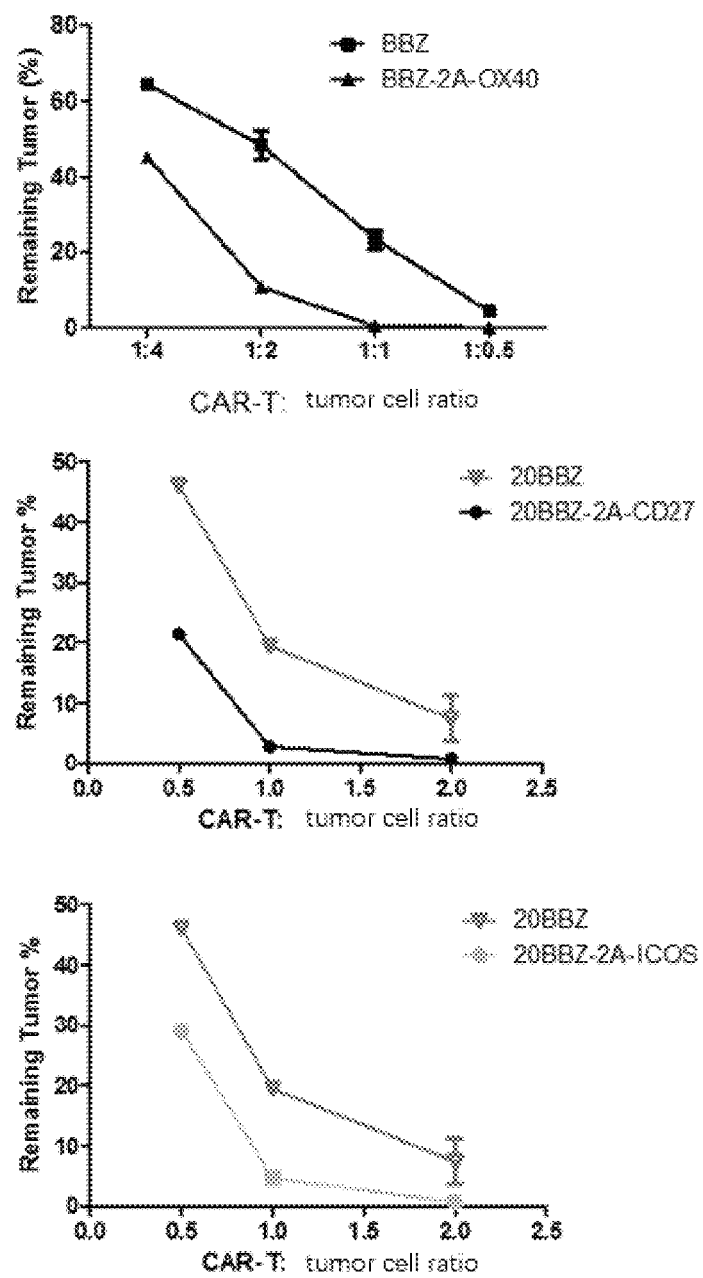
FIG. 13 is a schematic view showing the tumor killing ability of BBZ CAR-T cell and BBZ-2A-OX40 CAR-T cell in an embodiment of the present invention.

Example 7—Comparison of Tumor-Killing Abilities of 20BBZ CAR-T Cell and 20BBZ-2A-OX40 CAR-T Cell 20BBZ CAR-T cell and 20BBZ-2A-OX40 CAR-T cell obtained in Step 2 of Example 1, 20BBZ-2A-ICOS CAR-T cell obtained in Step 2 of Example 3, and 20BBZ-2A-CD27 CAR-T cell obtained in Step 2 of Example 4 were inoculated into a 96-well plate, and Raji tumor cells were added at a CAR-T:tumor cell ratio of 1:1, 1:2, 1:4. After 24 and 48 hours, the survival rates of tumor cells were compared, and the results are shown in FIG. 13. It can be seen from the figure that 20BBZ-2A-OX40/ICOS/CD27 CAR-T cell has similar tumor killing ability as compared with 20BBZ CAR-T cell, and some CAR-T including the co-stimulatory receptor has a stronger tumor killing ability.

Figure 14:
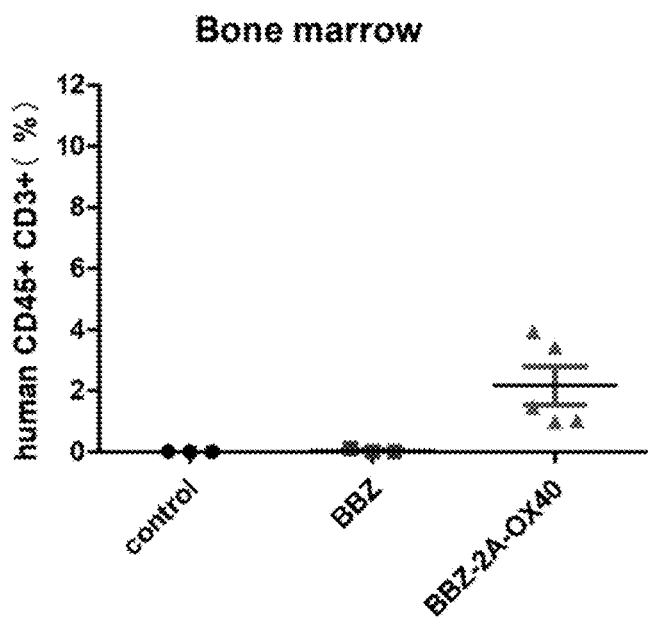
FIG. 14 is a schematic view showing the anti-tumor ability of BBZ CAR-T cell and BBZ-2A-OX40 CAR-T cell in an embodiment of the present invention.
Figure 15:
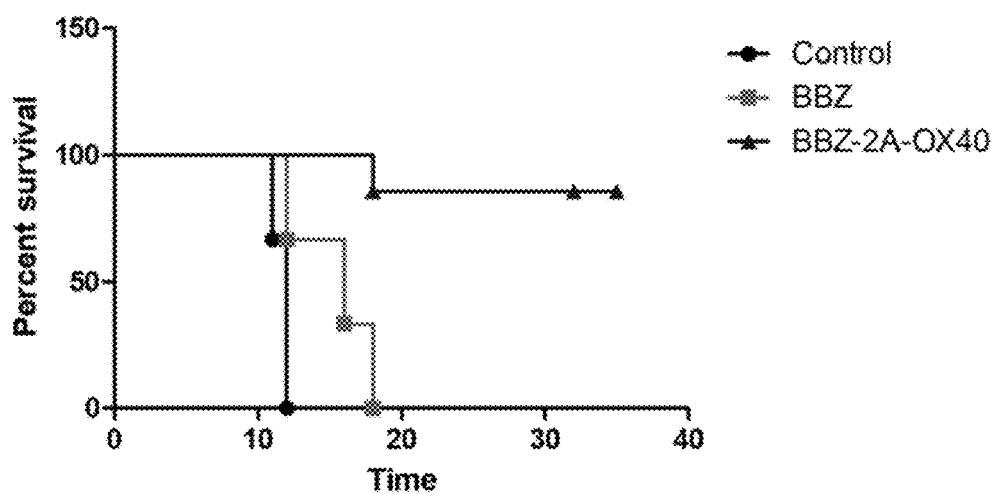
FIG. 15 is a schematic view showing the in vivo survival ability of BBZ CAR-T cell and BBZ-2A-OX40 CAR-T cell in an embodiment of the present invention.

Example 8—Comparison of Anti-Tumor Ability and In Vivo Survival Ability of 20BBZ CAR-T Cell and 20BBZ-2A-OX40 CAR-T Cell $10^6$ Nalm-6 tumor cells were intravenously inoculated into B-NDG mice, which were treated with $10^7$ 20BBZ CAR-T cells and 20BBZ-2A-OX40 CAR-T cells after 6 days. The mice were observed for their survival rates, and some mice were detected for the level of tumor cells and CAR-T cells in their marrow on Day 7. The results are shown in FIG. 14 and FIG. 15, respectively. It can be seen from the figure that 20BBZ-2A-OX40 CAR-T cell, as compared with 20BBZ CAR-T cell, significantly prolongs the survival of mice, and expanded more in vivo.

It can be seen from the aforesaid examples that the present invention constructs a novel CAR-T cell including a co-stimulatory receptor, which significantly increases the activation ability, survival ability, expansion ability of the CAR-T cells in tumors, as compared with the current CAR-T technology in clinic use, and has a more superior anti-tumor therapeutic effect.

Hereinbefore the specific embodiments of the present invention are described in details. However, they are only used as examples, and the present invention is not limited to the specific embodiments as described above. For those skilled in the art, any equivalent modifications and substitutions made to the present invention are encompassed in the scope of the present invention. Therefore, all the equal transformations and modifications without departing from the spirit and scope of the present invention should be covered in the scope of the present invention.

What is claimed is:

1. A fusion protein, which comprises, from N-terminus to C-terminus, (a) a chimeric antigen receptor (CAR) that specifically binds to a CD20, (b) a 2A peptide and (c) a OX40 protein wherein;
said fusion protein has a structure of scFv(X)-(H)-(TM)-(Y)CD3zeta-2A-(Z); the amino acid sequence of said scFv(X)-(H)-(TM)-(Y)CD3zeta comprises SEQ ID No.1; the amino acid sequence of said 2A peptide comprises SEQ ID No.7, SEQ ID No.8, SEQ ID No.9 or SEQ ID No.10; (Z) is OX40 and the amino acid sequence of said OX40 protein comprises SEQ ID No.2.

2. A CAR-T cell comprising;
an expression vector, wherein the expression vector comprises a nucleic acid encoding said fusion protein of claim 1.

3. A method of preparing said CAR-T cell of claim 2, comprising the following steps:
step 1:
incorporating a nucleic acid encoding the 2A peptide between a nucleic acid encoding the CAR and a nucleic acid encoding the OX40 protein to form a nucleic acid encoding the fusion protein, adding a lentiviral vector to both ends of the nucleic acid encoding the fusion protein, and co-transfecting with a lentiviral packaging plasmid to obtain a virus comprising the nucleic acid encoding the fusion protein; and
step 2:
culturing purified human PBMC, and infecting said PBMC with the virus comprising the nucleic acid encoding the fusion protein obtained in step 1, subjecting the infected PBMC to cell expansion under suitable conditions to prepare the CAR-T cell.

4. The method of preparing said CAR-T cell according to claim 3, comprising:
incorporating the nucleic acid encoding 2A peptide between the nucleic acid encoding the CAR and the nucleic acid encoding the OX40 protein by overlap PCR to form the nucleic acid encoding the fusion protein, and adding restriction sites to both ends of the nucleic acid encoding the fusion protein to clone a lentiviral vector; subjecting the clones sequenced correctly to a large scale endotoxin-free extraction, and co-transfecting with the lentiviral packaging plasmid; after a predetermined time period, collecting a supernatant, filtering, and centrifuging to concentrate the virus to obtain a virus comprising the nucleic acid encoding the fusion protein.

5. The method of preparing said CAR-T cell according to claim 3, wherein the step 2 comprises: isolating human PBMC for purification, inoculating into a culture plate under suitable stimulation conditions, culturing them for a predetermined period of time, infecting said PBMC with the virus comprising the nucleic acid encoding the fusion protein produced in step_1, and subjecting the infected PBMC to cell expansion under suitable stimulation conditions, after 2 rounds of expansion under stimulation, obtaining the CAR-T cell.

6. A method of treating a B cell lymphoma expressing CD20 in a human subject, comprising administrating to the subject a CAR-T cell comprising an expression vector comprising a nucleotide sequence encoding a fusion protein comprising, from N-terminus to C-terminus, a chimeric antigen receptor (CAR) that specifically binds to human CD20 which comprises SEQ ID NO: 1, a 2A peptide which comprises SEQ ID NO: 7, SEQ ID NO: 8, SEQ ID NO: 9, or SEQ ID NO: 10, and a costimulatory protein which comprises SEQ ID NO: 2.

7. An expression vector, comprising a nucleotide sequence encoding the fusion protein of claim 1.

* * * * *

SEQUENCE LISTING

```
<160> NUMBER OF SEQ ID NOS: 10

<210> SEQ ID NO 1
<211> LENGTH: 468
<212> TYPE: PRT
<213> ORGANISM: Artificial Sequence
<220> FEATURE:
<223> OTHER INFORMATION: the sequence of scFv-antihCD20-20BBZ

<400> SEQUENCE: 1

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80
```

```
Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Gly Gly Gly Gly Ser Gly
            100                 105                 110

Gly Gly Gly Ser Gly Gly Gly Ser Gln Val Gln Leu Gln Gln Pro
        115                 120                 125

Gly Ala Glu Leu Val Lys Pro Gly Ala Ser Val Lys Met Ser Cys Lys
130                 135                 140

Ala Ser Gly Tyr Thr Phe Thr Ser Tyr Asn Met His Trp Val Lys Gln
145                 150                 155                 160

Thr Pro Gly Arg Gly Leu Glu Trp Ile Gly Ala Ile Tyr Pro Gly Asn
                165                 170                 175

Gly Asp Thr Ser Tyr Asn Gln Lys Phe Lys Gly Lys Ala Thr Leu Thr
            180                 185                 190

Ala Asp Lys Ser Ser Ser Thr Ala Tyr Met Gln Leu Ser Ser Leu Thr
        195                 200                 205

Ser Glu Asp Ser Ala Val Tyr Tyr Cys Ala Arg Ser Thr Tyr Tyr Gly
210                 215                 220

Gly Asp Trp Tyr Phe Asn Val Trp Gly Ala Gly Thr Thr Val Thr Val
225                 230                 235                 240

Ser Ala Ala Ala Ala Thr Thr Thr Pro Ala Pro Arg Pro Pro Thr Pro
                245                 250                 255

Ala Pro Thr Ile Ala Ser Gln Pro Leu Ser Leu Arg Pro Glu Ala Cys
            260                 265                 270

Arg Pro Ala Ala Gly Gly Ala Val His Thr Arg Gly Leu Asp Phe Ala
        275                 280                 285

Cys Asp Ile Tyr Ile Trp Ala Pro Leu Ala Gly Thr Cys Gly Val Leu
290                 295                 300

Leu Leu Ser Leu Val Ile Thr Leu Tyr Cys Lys Arg Gly Arg Lys Lys
305                 310                 315                 320

Leu Leu Tyr Ile Phe Lys Gln Pro Phe Met Arg Pro Val Gln Thr Thr
                325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
450                 455                 460

Leu Pro Pro Arg
465

<210> SEQ ID NO 2
<211> LENGTH: 277
<212> TYPE: PRT
```

<213> ORGANISM: Artificial Sequence
<220> FEATURE:
<223> OTHER INFORMATION: the sequence of OX40

<400> SEQUENCE: 2

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 3
<211> LENGTH: 283
<212> TYPE: PRT
<213> ORGANISM: Artificial Sequence
<220> FEATURE:
<223> OTHER INFORMATION: the sequence of HVEM

<400> SEQUENCE: 3

Met Glu Pro Pro Gly Asp Trp Gly Pro Pro Pro Trp Arg Ser Thr Pro
1               5                   10                  15

Lys Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45
```

```
Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Trp Trp Phe Leu Ser Gly
        195                 200                 205

Ser Leu Val Ile Val Ile Val Cys Ser Thr Val Gly Leu Ile Ile Cys
    210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
            260                 265                 270

Ile Pro Ser Phe Thr Gly Arg Ser Pro Asn His
        275                 280

<210> SEQ ID NO 4
<211> LENGTH: 199
<212> TYPE: PRT
<213> ORGANISM: Artificial Sequence
<220> FEATURE:
<223> OTHER INFORMATION: the sequence of ICOS

<400> SEQUENCE: 4

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125
```

```
His Ile Tyr Glu Ser Gln Leu Cys Cys Gln Leu Lys Phe Trp Leu Pro
    130                 135                 140
Ile Gly Cys Ala Ala Phe Val Val Cys Ile Leu Gly Cys Ile Leu
145                 150                 155                 160
Ile Cys Trp Leu Thr Lys Lys Lys Tyr Ser Ser Ser Val His Asp Pro
                165                 170                 175
Asn Gly Glu Tyr Met Phe Met Arg Ala Val Asn Thr Ala Lys Lys Ser
            180                 185                 190
Arg Leu Thr Asp Val Thr Leu
        195
```

<210> SEQ ID NO 5
<211> LENGTH: 260
<212> TYPE: PRT
<213> ORGANISM: Artificial Sequence
<220> FEATURE:
<223> OTHER INFORMATION: the sequence of CD27

<400> SEQUENCE: 5

```
Met Ala Arg Pro His Pro Trp Trp Leu Cys Val Leu Gly Thr Leu Val
1               5                   10                  15
Gly Leu Ser Ala Thr Pro Ala Pro Lys Ser Cys Pro Glu Arg His Tyr
            20                  25                  30
Trp Ala Gln Gly Lys Leu Cys Cys Gln Met Cys Glu Pro Gly Thr Phe
        35                  40                  45
Leu Val Lys Asp Cys Asp Gln His Arg Lys Ala Ala Gln Cys Asp Pro
    50                  55                  60
Cys Ile Pro Gly Val Ser Phe Ser Pro Asp His His Thr Arg Pro His
65                  70                  75                  80
Cys Glu Ser Cys Arg His Cys Asn Ser Gly Leu Leu Val Arg Asn Cys
                85                  90                  95
Thr Ile Thr Ala Asn Ala Glu Cys Ala Cys Arg Asn Gly Trp Gln Cys
            100                 105                 110
Arg Asp Lys Glu Cys Thr Glu Cys Asp Pro Leu Pro Asn Pro Ser Leu
        115                 120                 125
Thr Ala Arg Ser Ser Gln Ala Leu Ser Pro His Pro Gln Pro Thr His
    130                 135                 140
Leu Pro Tyr Val Ser Glu Met Leu Glu Ala Arg Thr Ala Gly His Met
145                 150                 155                 160
Gln Thr Leu Ala Asp Phe Arg Gln Leu Pro Ala Arg Thr Leu Ser Thr
                165                 170                 175
His Trp Pro Pro Gln Arg Ser Leu Cys Ser Ser Asp Phe Ile Arg Ile
            180                 185                 190
Leu Val Ile Phe Ser Gly Met Phe Leu Val Phe Thr Leu Ala Gly Ala
        195                 200                 205
Leu Phe Leu His Gln Arg Arg Lys Tyr Arg Ser Asn Lys Gly Glu Ser
    210                 215                 220
Pro Val Glu Pro Ala Glu Pro Cys Arg Tyr Ser Cys Pro Arg Glu Glu
225                 230                 235                 240
Glu Gly Ser Thr Ile Pro Ile Gln Glu Asp Tyr Arg Lys Pro Glu Pro
                245                 250                 255
Ala Cys Ser Pro
            260
```

<210> SEQ ID NO 6
<211> LENGTH: 255

```
<212> TYPE: PRT
<213> ORGANISM: Artificial Sequence
<220> FEATURE:
<223> OTHER INFORMATION: the sequence of 4-1BB

<400> SEQUENCE: 6

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 7
<211> LENGTH: 22
<212> TYPE: PRT
<213> ORGANISM: Artificial Sequence
<220> FEATURE:
<223> OTHER INFORMATION: the sequence of 2A

<400> SEQUENCE: 7

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 8
<211> LENGTH: 21
<212> TYPE: PRT
<213> ORGANISM: Artificial Sequence
<220> FEATURE:
<223> OTHER INFORMATION: the sequence of 2A
```

```
<400> SEQUENCE: 8

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 9
<211> LENGTH: 23
<212> TYPE: PRT
<213> ORGANISM: Artificial Sequence
<220> FEATURE:
<223> OTHER INFORMATION: the sequence of 2A

<400> SEQUENCE: 9

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 10
<211> LENGTH: 25
<212> TYPE: PRT
<213> ORGANISM: Artificial Sequence
<220> FEATURE:
<223> OTHER INFORMATION: the sequence of 2A

<400> SEQUENCE: 10

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```